(12) United States Patent
Veasey et al.

(10) Patent No.: US 9,375,534 B2
(45) Date of Patent: Jun. 28, 2016

(54) DRIVE MECHANISM FOR A DRUG DELIVERY DEVICE

(75) Inventors: Robert Veasey, Leamington Spa (GB); Simon Lewis Bilton, Leamington Spa (GB); Christopher Jones, Tewkesbury (GB); Garen Kouyoumjian, Leamington Spa (GB); Catherine Anne MacDonald, Ashby-de-la-Zouch (GB)

(73) Assignee: SANOFI-AVENTIS DEUTSCHLAND GMBH, Frankfurt am Main (DE)

( * ) Notice: Subject to any disclaimer, the term of this patent is extended or adjusted under 35 U.S.C. 154(b) by 1105 days.

(21) Appl. No.: 13/496,536

(22) PCT Filed: Sep. 29, 2010

(86) PCT No.: PCT/EP2010/064399
§ 371 (c)(1),
(2), (4) Date: Jul. 24, 2012

(87) PCT Pub. No.: WO2011/039208
PCT Pub. Date: Apr. 7, 2011

(65) Prior Publication Data
US 2012/0283648 A1 Nov. 8, 2012

(30) Foreign Application Priority Data

Sep. 30, 2009 (EP) ..................... 09171741

(51) Int. Cl.
*A61M 5/00* (2006.01)
*A61M 5/24* (2006.01)
(Continued)

(52) U.S. Cl.
CPC .............. *A61M 5/24* (2013.01); *A61M 5/31555* (2013.01); *A61M 5/31561* (2013.01);
(Continued)

(58) Field of Classification Search
CPC .............. A61M 5/24; A61M 5/31551; A61M 5/31541; A61M 5/31585; A61M 5/3155; A61M 2005/2407
USPC .................................. 604/207–209, 211, 218
See application file for complete search history.

(56) References Cited

U.S. PATENT DOCUMENTS 6,004,297 A * 12/1999 Steenfeldt-Jensen  A61M 5/31551
604/207
6,231,550 B1   5/2001 Laughlin
(Continued)

FOREIGN PATENT DOCUMENTS

DE   10237258     3/2004
JP   2002-501790  1/2002
(Continued)

OTHER PUBLICATIONS

Japanese Office Action issued for JP App. No. 2012-531376, mailed Jul. 29, 2014.
(Continued)

*Primary Examiner* — Phillip Gray
(74) *Attorney, Agent, or Firm* — McDonnell Boehnen Hulbert & Berghoff LLP

(57) ABSTRACT

A first output member is rotatable around an axis relatively to the body. A second output member is movable relatively to the body along the axis. The first output member and the second output member are rotationally coupled. A drive feature is provided to generate a rotation of the first output member. A part which is removable from and attachable to the body is provided so that the first output member is unidirectionally rotationally coupled with the drive feature when the part is attached to the body.

14 Claims, 4 Drawing Sheets

(51) Int. Cl.
 A61M 5/315 (2006.01)
 A61M 5/31 (2006.01)
(52) U.S. Cl.
 CPC ...... *A61M 5/31593* (2013.01); *A61M 5/31541* (2013.01); *A61M 5/31558* (2013.01); *A61M 5/31575* (2013.01); *A61M 2005/2407* (2013.01); *A61M 2005/2488* (2013.01); *A61M 2005/3142* (2013.01)

(56) References Cited

U.S. PATENT DOCUMENTS

2006/0184117 A1 8/2006 Knight et al.
2009/0062748 A1 3/2009 Moller et al.

FOREIGN PATENT DOCUMENTS

| JP | 2008-526455 | 7/2008 |
| JP | 2009-529396 | 8/2009 |
| WO | 99/38554 | 8/1999 |
| WO | 01/72361 | 10/2001 |
| WO | 2006/126902 | 11/2006 |

OTHER PUBLICATIONS

European Search Report for EP App. No. 09171741, completed Mar. 10, 2010.
International Search Report for International App. No. PCT/EP2010/064399, completed Apr. 7, 2011.
International Preliminary Report on Patentability for International App. No. PCT/EP2010/064399, completed Sep. 22, 2011.

* cited by examiner

DRIVE MECHANISM FOR A DRUG DELIVERY DEVICE

CROSS REFERENCE TO RELATED APPLICATIONS

The present application is a U.S. National Phase Application pursuant to 35 U.S.C. §371 of International Application No. PCT/EP2010/064399 filed Sep. 29, 2010, which claims priority to European Patent Application No. 09171741.3 filed on Sep. 30, 2009. The entire disclosure contents of these applications are herewith incorporated by reference into the present application.

FIELD OF INVENTION

The present invention relates to a drive mechanism for a drug delivery device.

BACKGROUND

Portable drug delivery devices are used for the administration of a drug that is suitable for self-administration by a patient. A drug delivery device is especially useful in the shape of a pen, which can be handled easily and kept everywhere available.

A type of drug delivery device is constructed to be refillable and reusable many times. A drug is delivered by means of a drive mechanism, which may also serve to set the dose or amount to be delivered.

DE 102 37 258 B4 describes a drug delivery device in the shape of an injection pen having a drive mechanism, which allows to deliver a plurality of different prescribed doses. The drive mechanism comprises elements which are rotated relatively to one another around a common axis.

SUMMARY

It is an object of the present invention to facilitate provision of a new drive mechanism for a drug delivery device or of a new drug delivery device.

This object is achieved by a drive mechanism according to claim 1. Further objects are achieved by variants and embodiments according to the dependent claims.

The drive mechanism for a drug delivery device comprises a body having a distal end and a proximal end, which are spaced apart in the direction of an axis. A first output member is arranged within the body, the first output member being rotatable around the axis relatively to the body. A second output member is arranged within the body along the axis, the second output member being movable relatively to the body along the axis. The first output member and the second output member are rotationally coupled. A drive feature, which may comprise input members, is provided to generate a rotation of the first output member. A part which is removable from and attachable to the body is provided so that the first output member is unidirectionally rotationally coupled with the drive feature when the part is attached to the body.

The term "drug", as used herein, preferably means a pharmaceutical formulation containing at least one pharmaceutically active compound, wherein in one embodiment the pharmaceutically active compound has a molecular weight up to 1500 Da and/or is a peptide, a protein, a polysaccharide, a vaccine, a DNA, a RNA, an enzyme, an antibody, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exedin-3 or exedin-4 or an analogue or derivative of exedin-3 or exedin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:
H-(Lys)4-des Pro36, des Pro37 Exendin-4(1-39)-NH2,
H-(Lys)5-des Pro36, des Pro37 Exendin-4(1-39)-NH2,
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39), wherein the group -Lys6-NH2 may be bound to the C-terminus of the Exendin-4 derivative;
or an Exendin-4 derivative of the sequence
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4 (1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4 (1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp(O2) 25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2)25, Asp28] Exendin-4(S1-39)-(Lys)6-NH2,
H-Asn-(Glu)5-des Pro36, Pro37, Pro38 [Met(O)14, Trp(O2) 25, Asp28] Exendin-4(1-39)-(Lys)6-NH2;
or a pharmaceutically acceptable salt or solvate of any one of the afore-mentioned Exedin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

The body can be any housing or any component that forms part of a housing, for example. The body can also be some kind of an insert connected with an exterior housing. The body may be designed to enable the safe, correct, and/or easy handling of the device and/or to protect it from harmful liquids, dust or dirt. The body can be unitary or a multipart component of tubular or non-tubular shape. The body may house a cartridge, from which doses of a drug can be dispensed. The body can especially have the shape of an injection pen.

The term "distal end" refers to a part of the body or housing which is intended to be arranged at a portion of the drug delivery device from which a drug is dispensed. The term "proximal end" refers to a part of the body or housing which is remote from the distal end. The term "distal direction" refers to a movement in the same direction as a movement from the proximal end towards the distal end, not specifying a point of departure nor an end point, so that the movement may go beyond the distal end. The term "proximal direction" refers to a movement in the direction opposite to the distal direction.

The drive mechanism can be used to expel a drug from a receptacle or cartridge inserted in the body of a drug delivery device. The drug delivery device can be a disposable or re-usable device designed to dispense a dose of a drug, especially a liquid, which may be insulin, a growth hormone, a heparin, or an analogue and/or a derivative thereof, for example. The drug may be administered by a needle, or the device may be needle-free. The device may be further designed to monitor physiological properties like blood glucose levels, for example. Each time the second output member is shifted in the distal direction with respect to the body, a dose of the drug is expelled from the drug delivery device.

In an embodiment of the drive mechanism, the first output member is an output sleeve, and the second output member is an output shaft.

In a further embodiment, a resilient element is provided, which is restrained by the removable and attachable part when the part is attached to the body. The resilient element removes the unidirectional rotational coupling when the removable and attachable part is removed from the body, so that the first output member is rotatable in an opposite direction.

In a further embodiment, the removable and attachable part is a cartridge holder provided at the distal end of the body.

In a further embodiment, a pinion member rotationally couples the first output member and the drive feature.

In a further embodiment, a pawl member allows a rotation of the first output member in only one direction when the removable and attachable part is attached to the body, and allows a rotation of the first output member in an opposite direction when the removable and attachable part is removed from the body.

In a further embodiment, the pinion member has notches, and the pawl member is a hinged tongue or a resilient or resiliently mounted cantilever. The pawl member has a tip or edge that engages the notches, thus preventing rotation of the pinion member in one direction. The pawl member is permanently disengaged from the notches when the removable and attachable part is removed from the body.

In a further embodiment, a first input member is arranged within the body parallel to the axis along a further axis, the first input member being movable relatively to the body along the further axis. A second input member is arranged within the body, the second input member being rotatable around the further axis relatively to the body. The first input member and the second input member are coupled by a screw thread. A clutch rotationally locks the second input member with the pinion member when a load is exerted on the second input member in the distal direction, and does not lock the second input member with the pinion member when no load is exerted on the second input member in the distal direction.

In a further embodiment, a shift of the first input member in the distal direction generates a rotation of the second input member. The rotation of the second input member generates a rotation of the first output member. The rotation of the first output member generates a shift of the second output member in the distal direction.

In a further embodiment, a set operation is performed by shifting the first input member in the proximal direction, while the second input member is not locked with the pinion member.

In a further embodiment, a reset operation is performed, after the removable and attachable part has been removed from the body, by shifting the second output member in the proximal direction.

In a further embodiment, a last-dose nut is arranged within the body, the last-dose nut being movable relatively to the body along the further axis. The last-dose nut is coupled with the second input member by a further screw thread and is rotationally coupled with the first output member. The second input member rotates relatively to the last-dose nut when the first input member is shifted in the proximal direction. This is due to the fact that the second input member is not locked with the pinion member and consequently not locked to the first output member, and a movement of the last-dose nut in the distal or proximal direction is generated by means of the further screw thread. The body, the first output member or the second input member are provided with a stop element limiting the movement of the last-dose nut in the distal or the proximal direction. The stop element may be a protruding part of the second input member, for example.

In a further embodiment, a reset operation is performed by shifting the second output member in the proximal direction, the first output member rotating according to the rotational coupling to the second output member. The rotation of the first output member generates a rotation of the last-dose nut. The rotation of the last-dose nut relatively to the second input member generates a movement of the last-dose nut in the distal or proximal direction.

In a further embodiment, the first output member and the second output member are coupled by a screw thread. This screw thread and the further screw thread are provided with pitches that are adapted to the rotational coupling of the last-dose nut with the first output member in such a manner as to produce a movement of the last-dose nut to a start position during a reset operation. The start position has a defined distance from the protruding part of the second input member.

In a further embodiment, a groove or track of the body locks the second output member rotationally to the body while allowing a shift of the second output member along the axis.

An embodiment of the drive mechanism and its operation are described in the following as an example. A first output member of the drive mechanism is formed by an output sleeve, and a second output member is formed by an output shaft. The first output member is rotated by means of the input drive feature. The drive feature can comprise a first input member, formed by an input shaft, and a second input member, formed by an input sleeve. The input members are arranged along a first axis, and the output members are arranged along a second axis, parallel to the first axis. The input members and the output members are coupled by a kind of gear, which allows a unidirectional rotation of the output members. This can be achieved by an arrangement of a pinion member and a pawl member functioning in the manner of a ratchet. The pawl can be released from the pinion so that the output members are free to rotate in both directions. A clutch coupling the first input member and the second input member is provided to enable the user to set a dose without rotating the output members and to deliver a dose of the drug while the clutch is engaged and an output member rotates simultaneously with the second input member. The gear arrangement allows the second input member and the first output member to rotate at different speeds.

In the following, examples and embodiments of the drive mechanism are described in detail in conjunction with the appended figures.

DETAILED DESCRIPTION

Figure 1:
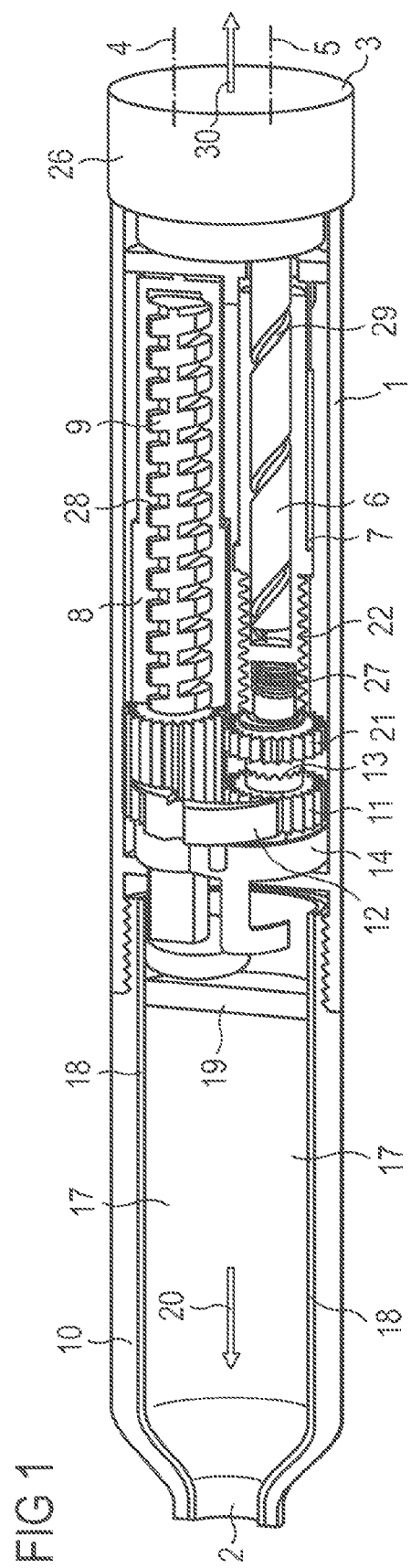
FIG. 1 shows a perspective cut-away view of an injection pen comprising an embodiment of the drive mechanism.

FIG. 1 shows a cross-section of an injection pen comprising a drive mechanism having input and output members. The body 1 has a distal end 2 and a proximal end 3. Output members of the drive mechanism are arranged along a first axis 4. Input members of the drive mechanism are arranged along a second axis 5, which is parallel to the first axis 4. A first input member 6 is formed by a shaft in this embodiment. The first input member 6 is coupled with a second input member 7, which is an input sleeve in this embodiment. The first input member 6 and the second input member 7 form an input drive feature of the drive mechanism. The coupling of the first input member 6 and the second input member 7 can be achieved by a screw thread 29. The first input member 6 is provided for an operation by the user and juts out of the body 1 at its proximal end 3. There, the first input member 6 is preferably provided with a grip 26, which can be used to pull the first input member 6 out of the body 1 in the proximal direction 30. The screw thread 29 coupling the first input member 6 with the second input member 7 makes the second input member 7, formed by the input sleeve, rotate with respect to the first input member 6 around the second axis 5 and thus relatively to the body 1. An axial movement of the second input member 7 in the distal direction or in the proximal direction is inhibited by suitable components of the drive mechanism or the body 1, like protruding elements, webs or the like. The second input member 7 therefore stays at its position and merely rotates around the second axis 5.

The second input member 7 is coupled with the first output member 8 by means of a unidirectional gear like a ratchet. The gear comprises a pinion member 11 and a pawl member 12. The pawl member 12 can be a hinged tongue or a kind of cantilever having a hook or edge engaging notches in a toothed circumference of the pinion member 11, for example. The pinion member 11 is coupled with the second input member 7 by means of a clutch 13, so that the pinion member 11 can be released from the second input member 7 to prevent the pinion member 11 from rotating simultaneously with the second input member 7. A clutch spring 27 can be provided to disengage the clutch 13 as long as the first input member 6 is not pushed in the distal direction 20. Therefore, the pinion member 11 does not rotate together with the second input member 7 when the first input member 6 is shifted in the proximal direction 30. Only when the first input member 6 is pushed in the distal direction 20 and the clutch spring 27 is compressed, the clutch 13 engages, and the pinion member 11 rotates according to the rotation of the second input member 7. Then, the pinion member 11 drives the first output member 8, which can be coupled to the pinion member 11 by means of a gear wheel forming an integral part of the first output member 8 or by means of a similar device. The pawl member 12 allows the rotation of the pinion member 11 in one rotational direction only, and consequently the rotation of the first output member 8 is restricted to the corresponding rotational direction according to the coupling between the pinion member 11 and the first output member 8.

A second output member 9 is coupled with the first output member 8. The coupling can be achieved by a further screw thread 28, for example. The first output member 8 can be an output sleeve, and the second output member 9 can be an output shaft. The coupling between the first output member 8 and the second output member 9 is such that the rotation of the first output member 8 allowed by the pawl member 12 drives the second output member 9 in the distal direction 20. The second output member 9 can be used as a piston rod or plunger driving a piston 19 in the distal direction 20. The piston 19 is provided to expel a drug from a receptacle, particularly from a cartridge 18, which is inserted in a dedicated compartment 17 at the distal end 2 of the body 1. If the body 1 is provided with a removable and attachable part 10 at its distal end 2, the cartridge 18 can be removed and exchanged with a new one, and the device can easily be refilled. This enables the drug delivery device to be reused.

After a cartridge 18 has been emptied, the removable and attachable part 10 is removed from the body 1 and the empty cartridge 18 taken out of the compartment 17. The second output member 9 has to be shifted back to its initial position near the proximal end 3 of the body 1, before a full cartridge 18 comprising a piston 19 at a proximal position can be inserted. The first output member 8 is not shifted axially with respect to the body 1, and the second output member 9 is therefore shifted relatively to the first output member 8. Because of the coupling between the first output member 8 and the second output member 9, by means of the screw thread 28 for instance, the shift of the second output member 9 in the proximal direction 30 is accompanied with the rotation of the first output member 8 in the rotational direction that is not allowed by the pinion member 11 and the engaged pawl member 12. To make the shift of the second output member 9 possible, the pawl member 12 is disengaged from the pinion member 11, so that the pinion member 11 is free to rotate in both rotational directions.

A resilient element 14 can be provided to drive the pawl member 12 out of its engagement with the pinion member 11, when the removable and attachable part 10 is removed and the unidirectional gear is thus released. When the removable and attachable part 10 is attached, the resilient element 14 is restrained from its action on the pawl member 12. The pawl member 12 is preferably also resilient or at least resiliently mounted, so that the pawl member 12 is automatically re-engaged with the pinion member 11, when the removable and attachable part 10 is attached. This enables a reset operation to be performed after the removal of an emptied cartridge. The operation of the drive mechanism will now be described with reference to FIGS. 2 to 8.

Figure 2:
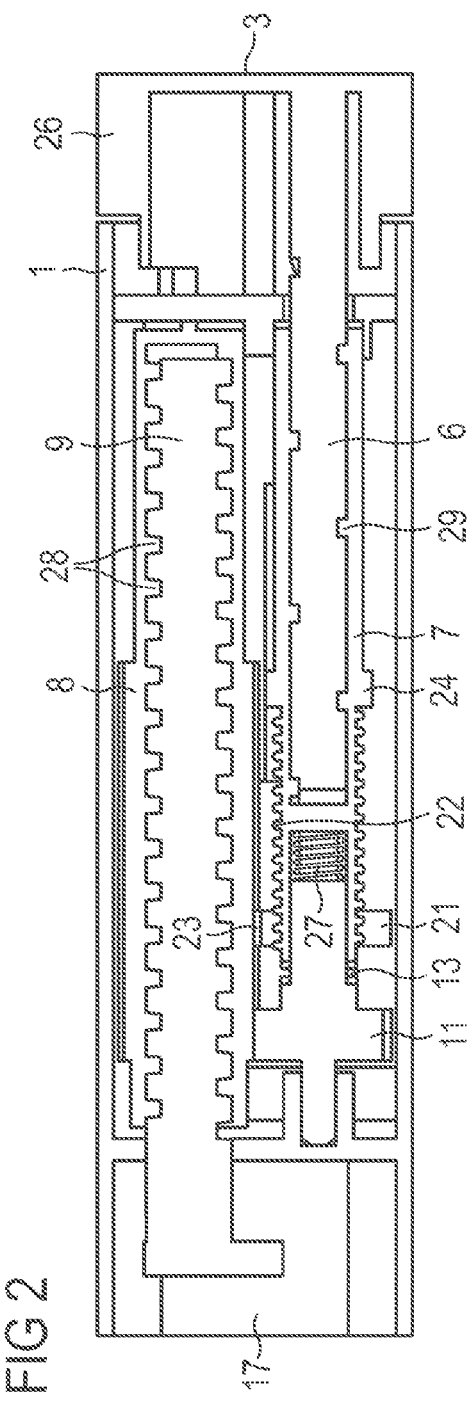
FIG. 2 shows a cross-section of the drive mechanism in a start position.

FIG. 2 shows a schematic cross-section of the drive mechanism in an initial state. The gear coupling the input drive feature and the output members is schematically represented by the pinion member 11 shown in cross-section. The removable and attachable part is attached, and the pawl member engages with the pinion member 11, restricting the rotation to one rotational direction. In this start position, a set operation can be performed by pulling the first input member 6 in the proximal direction.

Figure 3:
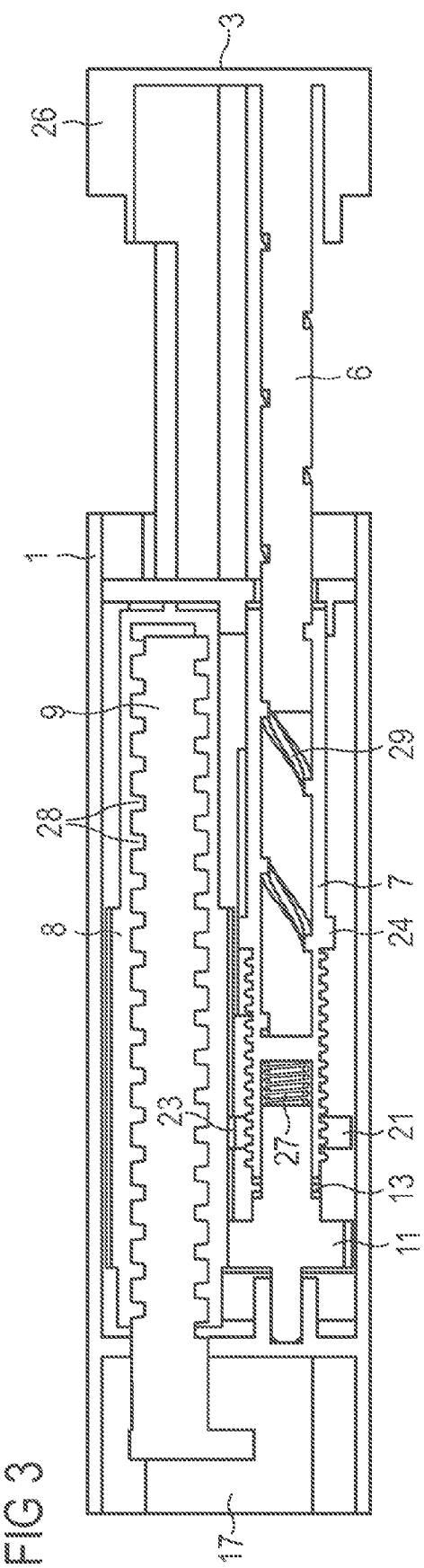
FIG. 3 shows a cross-section according to FIG. 2 after a set operation.

FIG. 3 shows a cross-section according to FIG. 2 after the set operation. The first input member 6 has been shifted in the proximal direction and sticks out of the body 1. The movement of the first input member 6 caused the second input member 7, the input sleeve, to rotate. The clutch 13 provided to couple the second input member 7 with the pinion member 11 is disengaged during the set operation. The pinion member 11 does therefore not rotate with the second input member 7. Consequently, the output members are not moved. In the state of the drive mechanism shown in FIG. 3, the set dose can be dispensed by just pushing the first input member 6 in the distal direction. This movement makes the clutch 13 engage, because the second input member 7 is pressed towards the pinion member 11 against the force of the clutch spring 27, compressing the clutch spring 27. The clutch 13 may be formed by an angular arrangement of teeth or the like. Instead of a toothed structure, the friction occurring between the surfaces of the second input member 7 and the pinion member 11, which are pressed together, may suffice to engage the pinion member 11 with the rotating second input member 7. As a result, the rotating pinion member 11 rotates the first output member 8. The coupling of the first output member 8 with the second output member 9 causes the second output member 9 to be shifted in the distal direction, thus driving the piston to expel the preset dose.

Figure 4:
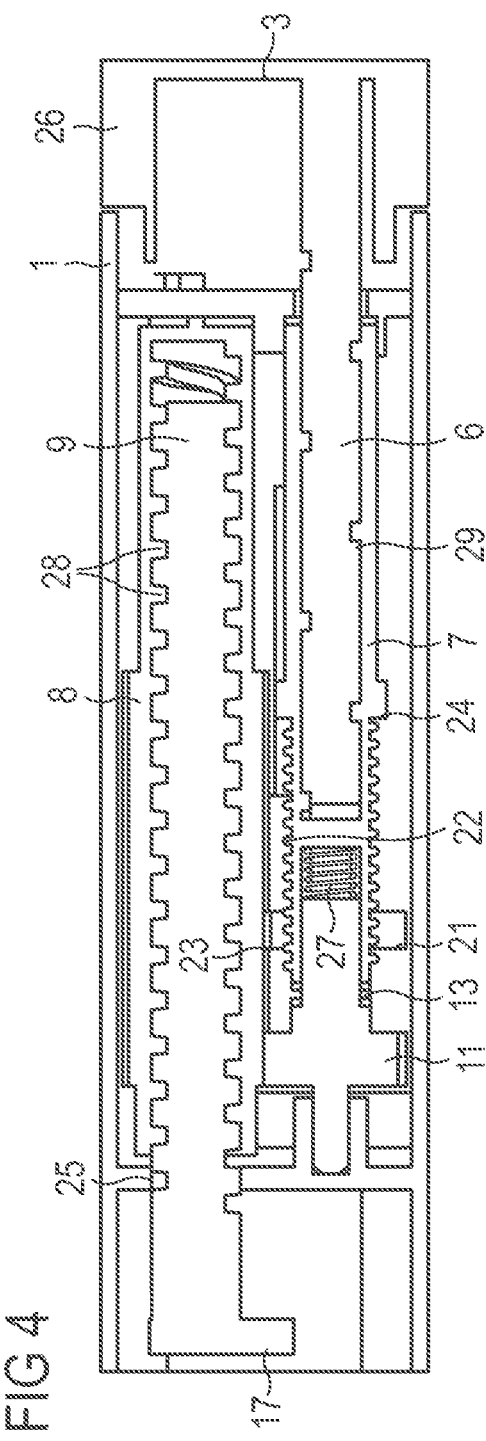
FIG. 4 shows a cross-section according to FIG. 3 after a dispense operation.

FIG. 4 shows the cross-section according to FIG. 3 after the delivery of the set dose. The state of the drive mechanism is now comparable to the initial state shown in FIG. 2, except for the second output member 9 having been shifted a small distance in the distal direction. A further dose can now be set and delivered, again by moving the second output member 9 by the defined distance in the distal direction. This process can be repeated until the cartridge is empty.

Figure 5:
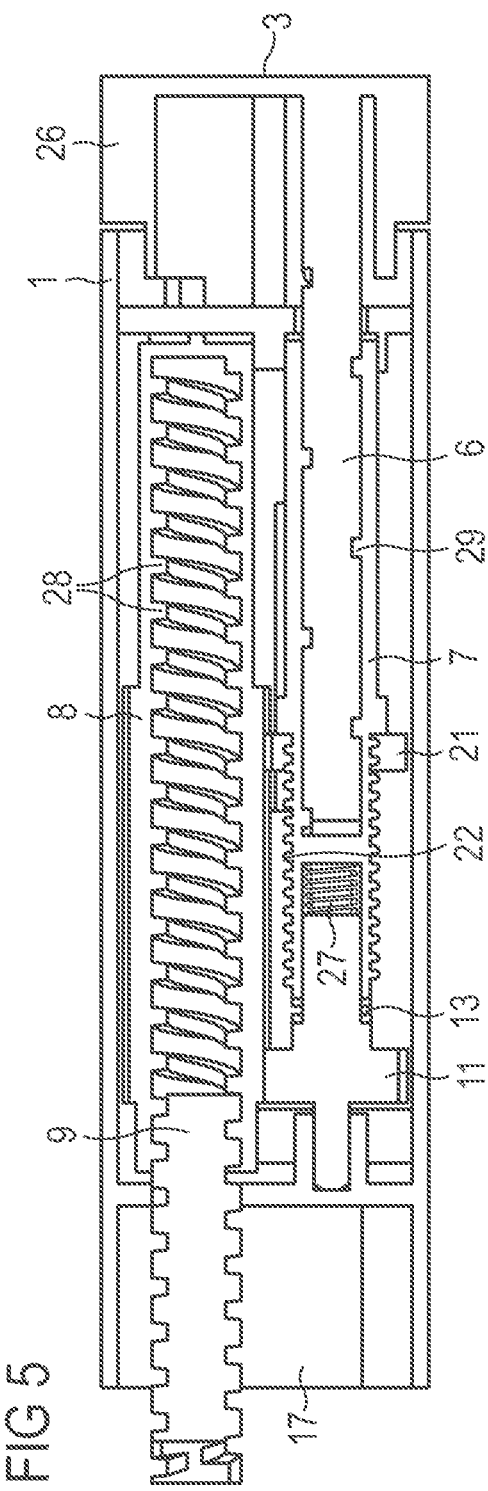
FIG. 5 shows a cross-section according to FIG. 4 after the delivery of a last dose.

FIG. 5 shows the position of the second output member 9 within the drive mechanism after the last dose of the drug has been dispensed. When the resilient element 14 is caused to disengage the pawl member 12 from the pinion member 11 by removing the removable and attachable part 10 from the main part of the body 1, the second output member 9 can be shifted in the proximal direction to its start position with the first output member 8 and the pinion member 11 freely rotating. The clutch 13 is disengaged, so that the second input member 7 does not rotate and, consequently, the first input member 6 is held stationary with respect to the body 1. In this way, the start position according to FIG. 2 is obtained.

A last-dose nut 21 may be provided to prevent the user from setting a dose when only an insufficient amount of the drug remains in the cartridge or when the cartridge is completely empty. The last-dose nut 21 is preferably in threaded engagement with the second input member 7, the input sleeve, shown by the schematically indicated screw thread 22 in FIGS. 2 to 5. The last-dose nut 21 is further in a gear tooth engagement 23 with the first output member 8, the output sleeve. During a set operation, the last-dose nut 21 advances along the input sleeve 7, in the proximal direction 30 in the example shown in the figures. This is due to the fact that the clutch 13 is not engaged during the set operation. Hence, the output sleeve 8 does not rotate and therefore, the last-dose nut 21 does not rotate either. During the dispense operation, the last-dose nut 21 does not advance relative to the input sleeve 7 in the axial direction, because the last-dose nut 21 is driven by the gear tooth engagement 23 to rotate with the output sleeve 8 at the same rotational rate as the input sleeve 7. The threads are appropriately designed to this effect.

In this operational concept, the last-dose nut 21 is moved in one direction, axially with respect to the body 1, during a set operation, while the last-dose nut 21 stays stationary in the axial direction during a dispense operation. The distance by which the last-dose nut 21 is shifted in each set operation is designed such that the last-dose nut 21 comes to a stop after the last dose has been expelled. To this purpose, the drive mechanism or the body can be provided with a stop feature, like a protruding part 24, to inhibit the further movement of the last-dose nut 21 in the axial direction. As the set operation can only be performed by a movement of the input shaft 6 which makes the input sleeve 7 rotate and thus the last-dose nut 21 be shifted in the axial direction, stopping the movement of the last-dose nut 21 inhibits a shift of the input shaft 6 and thus prevents the user from setting a further dose.

Figure 6:
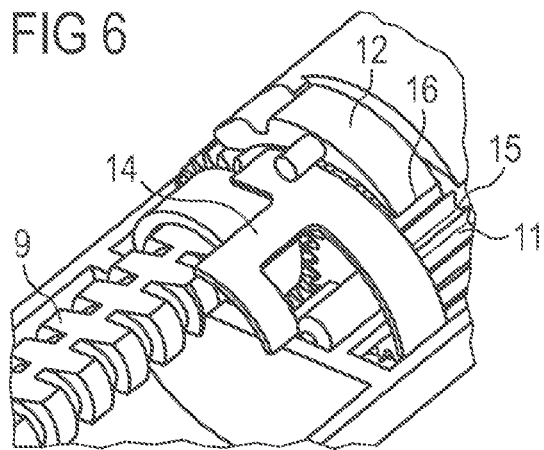
FIG. 6 shows a detail of the arrangement of the pinion member and the pawl member.

FIG. 6 shows the coupling between the drive feature and the output members by means of the pinion member 11 and the pawl member 12. The pawl member 12 is formed to be a hook or cantilever having a tip or edge 16 engaging notches 15 in the toothed pinion member 11. The resilient element 14 is kept away from the pawl member 12 by a protruding element or the like provided on the removable and attachable part 10. The pawl member 12 is therefore engaged with the pinion member 11, and a rotation of the pinion member 11 is only permitted in one rotational direction. This is the rotational direction that enables the second output member 9, the output shaft functioning as the piston rod, to be moved in the distal direction, but not be moved back in the proximal direction.

Figure 7:
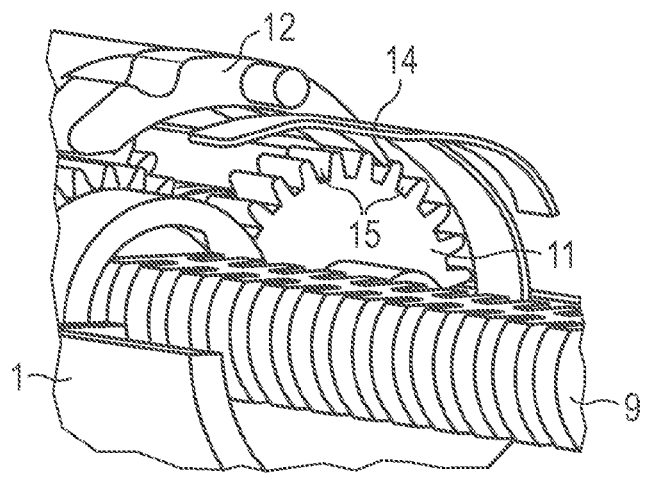
FIG. 7 shows another view of the arrangement of the pinion member with the pawl member engaged.

FIG. 7 shows the arrangement according to FIG. 6 in another perspective. The resilient element 14 is shown to be held at a distance from a protruding element of the pawl member 12. The pawl member 12 is therefore engaged with the pinion member 11. This can be achieved by the pawl member 12 being resiliently mounted. The pawl member 12 can be a plastic element, for instance, which is mounted to the drive mechanism or to the body in such a manner that the pawl member 12 occupies a position where a tip or edge 16 at the end of the pawl member 12 engages notches 15 between the teeth of the pinion member 11, when no external force is exerted on the pawl member 12.

Figure 8:
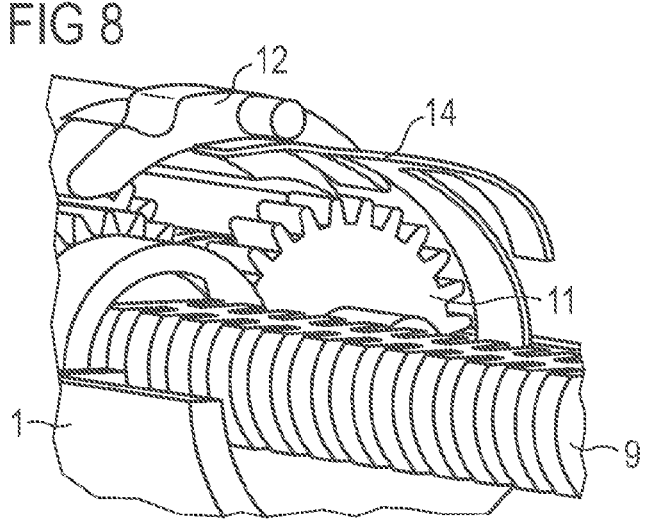
FIG. 8 shows the view according to FIG. 7 with the pawl member disengaged.

FIG. 8 shows the view according to FIG. 7 when the removable and attachable part 10 has been removed from the body 1, so that the resilient element 14 is free to relieve its tension and to come in contact with the protruding element of the pawl member 12. The resilient element 14 then pushes the pawl member 12 out of its engagement with the pinion member 11. This enables the second output member 9 to be shifted in the proximal direction, making the output sleeve 8 and the pinion member 11 rotate in the opposite rotational direction, which is now allowed by the release of the pawl member 12 from the pinion member 11.

The drive mechanism can be used in a wide range of reusable devices, particularly injection pens, and enables easy handling and an easy refill.

The invention claimed is:

1. Drive mechanism for a drug delivery device, comprising:
   a body having a distal end and a proximal end, which are spaced apart in the direction of an axis,
   a first output member arranged within the body, the first output member being rotatable around the axis relatively to the body,
   a second output member arranged within the body along the axis, the second output member being movable relatively to the body along the axis,
   the first output member and the second output member being rotationally coupled, and
   a drive feature that is provided to generate a rotation of the first output member,
   characterized in that
   the device further comprises a removable and attachable part, which is removable from and attachable to the body, the first output member being unidirectionally rotationally coupled with the drive feature when the part is attached to the body, so that the first output member is rotatable in one direction,
   a resilient element,
   the removable and attachable part restraining the resilient element when the part is attached to the body, and
   the resilient element removing the unidirectional rotational coupling when the removable and attachable part is removed from the body, so that the first output member is rotatable in an opposite direction.

2. The drive mechanism according to claim 1, wherein the first output member is an output sleeve, and the second output member is an output shaft.

3. The drive mechanism according to claim 1, wherein the removable and attachable part is a cartridge holder provided at the distal end of the body.

4. The drive mechanism according to claim 1, further comprising a pinion member rotationally coupling the first output member and the drive feature.

5. The drive mechanism according to claim 4, further comprising:
   a pawl member allowing a rotation of the first output member in only one direction when the removable and attachable part is attached to the body, and allowing a rotation of the first output member in an opposite direction when the removable and attachable part is removed from the body.

6. The drive mechanism according to claim 4, further comprising:
the pinion member having notches,
the pawl member being a hinged tongue or a resilient or resiliently mounted cantilever,
the pawl member having a tip or edge that engages the notches, thus preventing rotation of the pinion member in one direction, and
the pawl member being permanently disengaged from the notches when the removable and attachable part is removed from the body.

7. The drive mechanism according to claim 4, further comprising:
a first input member arranged within the body parallel to the axis along a further axis (5), the first input member being movable relatively to the body along the further axis,
a second input member arranged within the body, the second input member being rotatable around the further axis relatively to the body,
the first input member and the second input member being coupled by a screw thread, and
a clutch rotationally locking the second input member with the pinion member when a load is exerted on the second input member in the distal direction, and not locking the second input member with the pinion member when no load is exerted on the second input member in the distal direction.

8. The drive mechanism according to claim 7, wherein a shift of the first input member in the distal direction generates a rotation of the second input member, the rotation of the second input member generates a rotation of the first output member, and the rotation of the first output member generates a shift of the second output member in the distal direction.

9. The drive mechanism according to claim 7, wherein a set operation is performed by shifting the first input member in the proximal direction, while the second input member is not locked with the pinion member.

10. The drive mechanism according to claim 7, wherein a reset operation is performed, after the removable and attachable part has been removed from the body, by shifting the second output member in the proximal direction.

11. The drive mechanism according to claim 7, further comprising:
a last-dose nut arranged within the body, the last-dose nut being movable relatively to the body along the further axis,
the last-dose nut being coupled with the second input member by a further screw thread and being rotationally coupled with the first output member,
the second input member rotating relatively to the last-dose nut when the first input member is shifted in the proximal direction as the second input member is not locked with the pinion member and consequently not locked to the first output member, thus generating a movement of the last-dose nut in the distal or proximal direction by means of the further screw thread, and
a protruding part of the second input member, the protruding part limiting the movement of the last-dose nut in the distal or proximal direction.

12. The drive mechanism according to claim 11, wherein a reset operation is performed by shifting the second output member in the proximal direction, the first output member rotating according to the rotational coupling to the second output member,
the rotation of the first output member generates a rotation of the last-dose nut, and
the rotation of the last-dose nut relatively to the second input member generates a movement of the last-dose nut in the distal or proximal direction.

13. The drive mechanism according to claim 12, wherein the first output member and the second output member are coupled by a screw thread,
the screw thread coupling the output members and the further screw thread are provided with pitches that are adapted to the rotational coupling of the last-dose nut with the first output member in such a manner as to produce a movement of the last-dose nut to a start position during a reset operation, the start position having a defined distance from the protruding part of the second input member.

14. The drive mechanism according to claim 1, further comprising:
a groove or track of the body locking the second output member rotationally to the body while allowing a shift of the second output member along the axis.

* * * * *